United States Patent
Stenzel

(10) Patent No.: US 7,799,153 B2
(45) Date of Patent: Sep. 21, 2010

(54) METHODS AND APPARATUSES FOR MANUFACTURING MEDICAL DEVICES

(75) Inventor: Eric B. Stenzel, Tuam (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 916 days.

(21) Appl. No.: 11/282,989

(22) Filed: Nov. 18, 2005

(65) Prior Publication Data

US 2007/0114701 A1    May 24, 2007

(51) Int. Cl.
*B32B 37/00* (2006.01)

(52) U.S. Cl. .................. 156/64; 156/73.1; 156/580.1

(58) Field of Classification Search .................. 156/64, 156/73.1, 73.5, 82, 272.2, 359, 497, 499, 156/580.1, 580.2
See application file for complete search history.

(56) References Cited

U.S. PATENT DOCUMENTS

| | | | |
|---|---|---|---|
| 3,492,367 A * | 1/1970 | Starkweather, Jr. ........ 156/73.5 |
| 4,144,110 A * | 3/1979 | Luc ............................ 156/73.5 |
| 4,514,242 A * | 4/1985 | MacLaughlin et al. ..... 156/73.5 |
| 4,769,102 A * | 9/1988 | Neumuller et al. .......... 156/359 |
| 6,242,063 B1 | 6/2001 | Ferrera et al. |
| 6,520,399 B1 | 2/2003 | Salzer et al. |
| 6,596,217 B1 | 7/2003 | Davis-Lemessy et al. |
| 6,749,703 B2 * | 6/2004 | Iwashita et al. ................ 156/64 |
| 6,827,798 B1 * | 12/2004 | Ichikawa et al. ........... 156/73.1 |
| 2002/0068966 A1 | 6/2002 | Holman et al. |
| 2002/0144757 A1 | 10/2002 | Craig et al. |
| 2002/0165523 A1 | 11/2002 | Chin et al. |
| 2003/0018380 A1 | 1/2003 | Craig et al. |
| 2003/0077200 A1 | 4/2003 | Craig et al. |
| 2004/0131808 A1 | 7/2004 | Schoenle et al. |
| 2004/0181236 A1 | 9/2004 | Eidenschink et al. |
| 2005/0043679 A1 | 2/2005 | Devens, Jr. et al. |
| 2005/0228428 A1 | 10/2005 | Ali et al. |

FOREIGN PATENT DOCUMENTS

WO    WO 97/32624    9/1997

* cited by examiner

*Primary Examiner*—James Sells
(74) *Attorney, Agent, or Firm*—Crompton, Seager & Tufte, LLC

(57) ABSTRACT

Methods and apparatuses for manufacturing medical devices.

23 Claims, 3 Drawing Sheets

METHODS AND APPARATUSES FOR MANUFACTURING MEDICAL DEVICES

TECHNICAL FIELD

This invention relates to methods and apparatus for manufacturing medical devices.

BACKGROUND

Medical devices, such as balloon catheters, can be used to administer a variety of treatments. For example, in an angioplasty procedure, a balloon catheter can be used to widen a constricted bodily vessel, such as a coronary artery. A balloon catheter can also be used to deliver a tubular member, such as a stent, that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand or compact the stenosis radially so that the vessel can permit an increased rate of blood flow. After use, the balloon is collapsed and withdrawn.

In stent delivery, the stent is compacted on the balloon and transported to a target site. Upon reaching the site, the balloon can be expanded to deform and to fix the stent at a predetermined position, e.g., in contact with the vessel wall. The balloon can then be collapsed and withdrawn from the vessel.

SUMMARY

In one aspect of the invention, a method of manufacturing a medical device having a first portion and a second portion includes contacting the first portion and the second portion at a contact area, heating at least one of the first and second portions at the contact area, and vibrating at least one of the first and second portions at the contact area. At least one of the first and second portions of the medical device include one or more polymers.

In a further aspect, an apparatus for manufacturing a medical device includes a first member adapted to contact at least one of first and second medical device components, at least one of which includes one or more polymers. The first member is configured to transmit heat and vibratory energy to at least one of the first and second medical device components to bond the first and second medical device components to one another.

In another aspect of the invention, an apparatus for manufacturing a medical device includes a first member configured to bond a first polymeric portion of the medical device to a second polymeric portion of the medical device by heating and vibrating at least one of the first and second polymeric portions.

Embodiments may include one or more of the following features.

In certain embodiments, the heating and vibrating are performed simultaneously.

In some embodiments, the heating and vibrating are performed sequentially.

In certain embodiments, the heating and vibrating are performed by a single device.

In some embodiments, the first and second portions are contacted by applying pressure to at least one of the first and second portions.

In certain embodiments, the pressure is applied while heating and vibrating at least one of the first and second portions.

In some embodiments, the heating, vibrating, and pressure are performed by a single device.

In certain embodiments, the heating and vibrating are performed externally of the medical device.

In some embodiments, the heating and vibrating are performed within the medical device.

In certain embodiments, the heating and vibrating are performed within a lumen defined by the medical device.

In some embodiments, the method includes applying at least one of heat and vibratory energy to the first portion, and applying at least one of heat and vibratory energy to the second portion.

In certain embodiments, the method further includes applying pressure to at least one of the first and second portions.

In some embodiments, the method includes heating, vibrating, and applying pressure to the first portion.

In certain embodiments, heating at least one of the first and second portions involves contacting at least one of the first and second portions with a heated member.

In some embodiments, applying pressure to at least one of the first and second portions involves pressing a member against a surface of at least one of the first and second portions.

In certain embodiments, vibrating at least one of the first and second portions involves contacting at least one of the first and second portions with a vibrating member.

In some embodiments, the medical device comprises a balloon catheter.

In certain embodiments, the method further includes inserting a support member within a lumen defined by the balloon catheter.

In some embodiments, the method includes positioning the medical device between two opposed members, and at least one of the opposed members is configured to transmit at least one of heat and vibratory energy to at least one of the first and second portions.

In certain embodiments, the method includes contacting a member to the medical device, and the member is configured to transmit at least one of heat and vibratory energy to at least one of the first and second portions.

In some embodiments, the member includes a plate.

In certain embodiments, the member includes a roller.

In some embodiments, the vibrating step involves applying vibratory energy to at least one of the first and second portions.

In certain embodiments, the vibratory energy includes ultrasonic energy.

In some embodiments, the first and second portions are heated to a temperature that is less than a melting temperature of the one or more polymers of the first and second portions.

In certain embodiments, the method further includes detecting a temperature of a member configured to heat at least one of the first and second portions.

In some embodiments, the heating step includes applying heat to at least one of the first and second portions as a function of the detected temperature.

In certain embodiments, the apparatus further includes a second member, and the first and second members are configured to receive the first and second medical device components within a gap defined between the first and second members.

In some embodiments, the second member is configured to transmit at least one of heat, pressure, and vibratory energy to at least one of the first and second medical device components when the first and second medical device components are disposed within the gap.

In certain embodiments, the apparatus further includes a second member. The first and second members define a gap therebetween, and the first and second members are configured to receive the first and second polymeric portions of the medical device within the gap.

In some embodiments, the second member is configured to apply at least one of heat, pressure, and vibratory energy to at least one of the first and second polymeric portions of the medical device.

In certain embodiments, the first member includes a heating element.

In some embodiments, the first member includes a vibrator.

In certain embodiments, the first member includes an ultrasonic transducer.

In some embodiments, the first member includes a plate.

In certain embodiments, the first member comprises a roller.

In some embodiments, the apparatus further includes a temperature-detecting device.

In some embodiments, the temperature detecting device is configured to detect a temperature of the first member.

In certain embodiments, the temperature detecting device includes a thermocouple.

In some embodiments, the apparatus further includes a controller in communication with the temperature detecting device. The controller is adapted to maintain a temperature of the first and second portions within a predetermined temperature range.

In certain embodiments, the controller is adapted to maintain the heat at a temperature less than the melting point of the first and second polymeric portions.

In some embodiments, the apparatus includes multiple first members.

In certain embodiments, the first members include rollers.

In some embodiments, the first members include plates.

Embodiments may provide one or more of the following advantages.

In certain embodiments, the amount of heat applied to the medical device to bond the first and second portions is reduced relative to other bonding techniques (e.g., bonding techniques using only heat and pressure). This reduction of heat can help to reduce the amount of heat-related damage incurred by the first and/or second portions of the medical device in the contact area and/or in regions adjacent the contact area.

In some embodiments, heat, vibratory energy, and pressure are applied to the medical device via a single device. As a result, the speed and/or efficiency of the bonding process can be increased.

In certain embodiments, the medical device (e.g., the first and second portions of the medical device) is moved (e.g., rolled) relative to the apparatus during the bonding process. This movement of the medical device can help to ensure that all targeted regions of the medical device are bonded during the bonding process.

Other aspects, features, and advantages are in the description, drawings, and claims.

DETAILED DESCRIPTION

Figure 1:
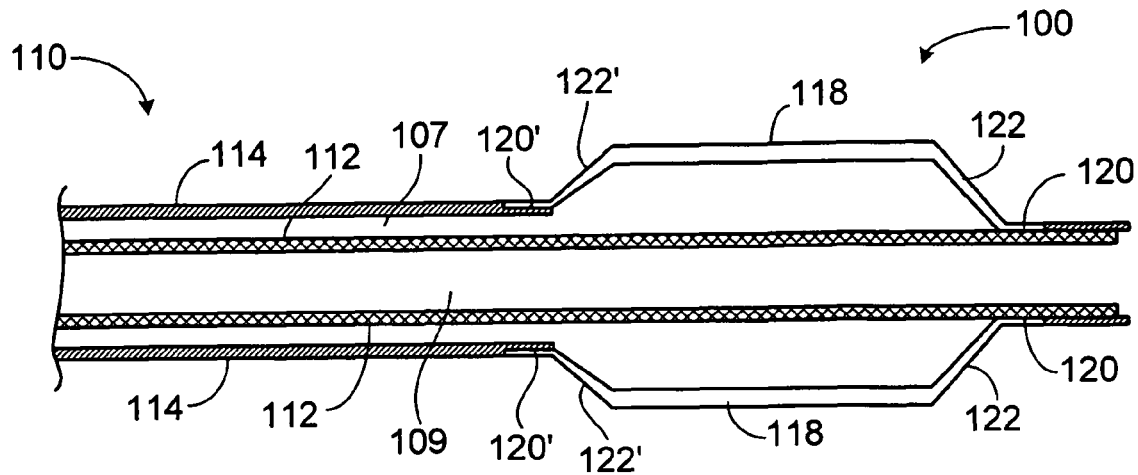
FIG. 1 is a partial, cross-sectional view of an embodiment of a balloon catheter.

Referring to FIG. 1, a balloon catheter 100 includes a balloon 105 carried by a catheter shaft assembly 110, which includes an inner member 112 and an outer member 114. An annular inflation lumen 107 extends between inner and outer members 112 and 114, from a proximal end of catheter shaft assembly 110 to a distal portion of catheter shaft assembly 110. A guidewire lumen 109 extends through inner member 112, from a proximal end of catheter shaft assembly 110 to a distal end of catheter shaft assembly 110. Balloon 105 includes a body portion 118, two waist portions 120 and 120', and two cone portions 122 and 122' that connect body portion 118 to waist portions 120 and 120', respectively. Waist portion 120 is attached (e.g., bonded) to a circumferential surface of a distal end region of inner member 112, and waist portion 120' is attached (e.g., bonded) to a circumferential surface of a distal end region of outer member 114. Balloon 105, inner member 112, and outer member 114 include (e.g., are formed of) one or more polymeric materials. For example, balloon 105 can include PET (polyethylene terephthalate), and inner and outer members 112 and 114 can include a polyester, such as Hytrel®. Other examples of balloon catheters are described in Patent Application Publication Nos. US 2002/0165523 and US 2005/0043679, which are incorporated by reference herein.

During use, balloon 105 can be positioned within a targeted region of a bodily vessel (e.g., a blood vessel) of a patient. Balloon 105 can, for example, be positioned within an occluded region of the vessel. After being positioned within the occluded region, balloon 105 can be inflated. Inflation of balloon 105 can help to dilate the occluded region of the vessel, which can increase the flow area of the vessel within the occluded region. The inflation of balloon 105 can alternatively or additionally function to release an endoprosthesis (e.g., a stent) within the occluded region of the vessel.

Waist portions 120 and 120' can be bonded to inner and outer members 112 and 114 by applying heat, vibratory energy, and pressure to waist portions 120 and 120'. Without wishing to be bound by theory, it is believed that by applying vibratory energy in addition to heat and pressure during the bonding process, the amount of heat-related damage experienced by balloon catheter 100 (e.g., by balloon 105 and inner and outer members 112 and 114) can advantageously be reduced relative to the use of heat and pressure alone and/or laser bonding, for example. The amount of heat-related damage can, for example, be reduced due to the localization of the applied energy relative to the energy applied during the use of heat and pressure alone and/or laser bonding techniques. By applying vibratory energy to waist portions 120 and 120' in addition to heat and pressure, the amount of heat applied to waist portions 120 and 120' can be reduced. Reducing the amount of heat applied to waist portions 120 and 120' can reduce the amount of heat-related damage incurred by waist portions 120 and 120' during the bonding process. Reducing the amount of heat applied to waist portions 120 and 120' can also reduce the amount of heat-related damage experienced by the regions of balloon 105 and inner and outer members 112 and 114 adjacent waist portions 120 and 120'. In certain embodiments, the structural integrity of the balloon material and/or the catheter shaft assembly material can be substantially maintained as a result.

Because similar apparatus and methods can be used to bond waist portion 120 and waist portion 120' to catheter shaft assembly 110, the following description focuses on the bonding of waist portion 120 only.

Figure 2:
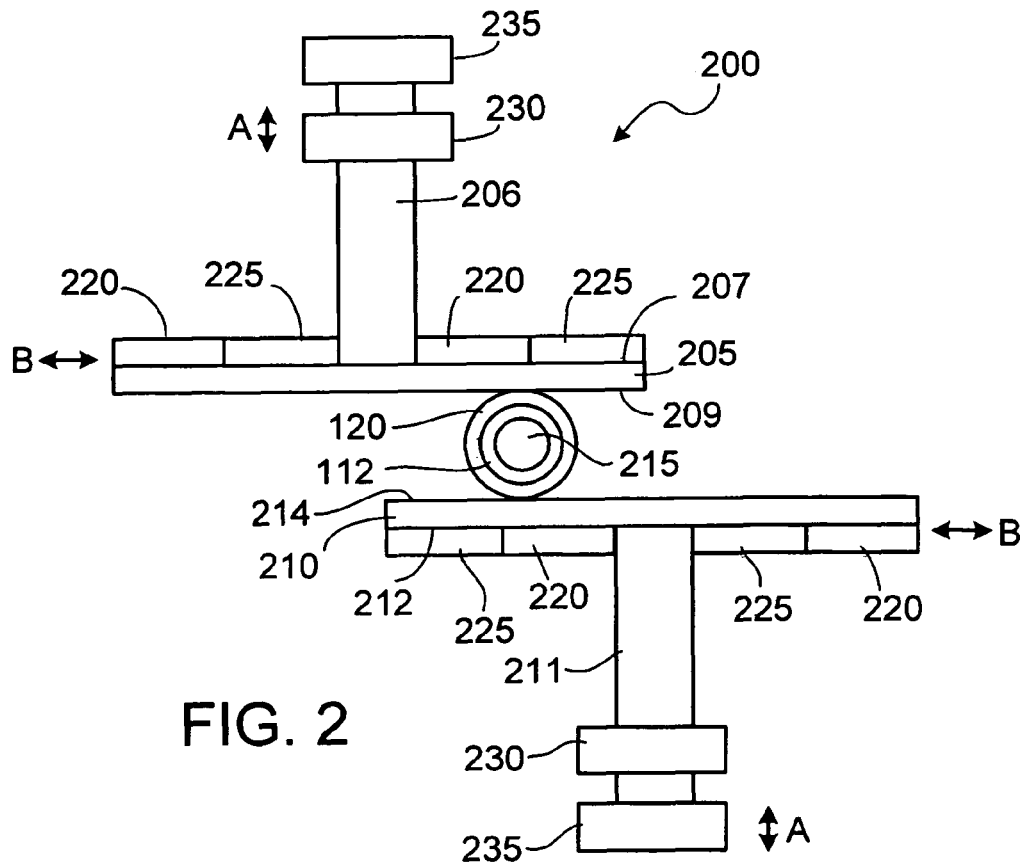
FIG. 2 illustrates an embodiment of a medical device manufacturing apparatus.

Referring to FIG. 2, an apparatus 200 that can be used to bond waist portion 120 to inner member 112 includes two opposed bonding plates 205 and 210. Multiple heaters (e.g., ceramic heaters) 220 and vibrators (e.g., ultrasonic transducers) 225 are attached to outer surfaces 207 and 212 of bonding plates 205 and 210, respectively. Heaters 220 and vibrators 225 are arranged in an alternating pattern about the length of plates 205 and 210. Heaters 220 and vibrators 225 can be attached to plates 205 and 210 using techniques such as welding techniques, bonding techniques, and/or adhesive techniques.

Support arms 206 and 211 extend from outer surfaces 207 and 212 of plates 205 and 210, respectively. Support arms 206 and 211 generally have sufficient strength to actuate plates 205 and 210 without substantially deforming or fracturing. In some embodiments, support arms 206 and 211 include one or more relatively durable materials, such as metals. Support arms 206 and 211 are operatively connected to a motor (e.g., a servomotor) 230, which can move plates 205 and 210 toward one another and away from one another. This movement of plates 205 and 210 is represented by arrow A in FIG. 2. Arm portions 206 and 211 are also operatively connected to a motor (e.g., a servomotor) 235 that can move plates 205 and 210 laterally relative to one another. This movement of plates 205 and 210 is represented by arrow B in FIG. 2.

Plates 205 and 210 can include one or more materials that are capable of transmitting heat, pressure, and vibratory energy. In some embodiments, plates 205 and 210 include one or more materials having a thermal conductivity level of 9.0 W/m-K or more (e.g., about 9.0 W/m-K to about 400 W/m-K). In some embodiments, plates 205 and 210 include one or more materials having a relatively high flexural strength (e.g., a flexural strength of about 100 MPa or more, about 100 MPa to about 900 MPa). Examples of materials that can be included in plates 205 and 210 include metals (e.g., stainless steel, titanium, aluminum, PERSS (as described in U.S. Published Patent Application Nos. 2003/0018380, 2002/0144757, and 2003/0077200), elgiloy, nitinol, hastalloy, and/or alloys including one or more of these materials) and ceramics (e.g., aluminum, silicon carbide, aluminum nitride, sapphire, cordierite, steatite, fosterite, titania, zirconia, cermet, quartz).

Heaters 220 can include one or more devices capable of heating plates 205 and 210. Examples of heaters include ceramic heaters (available from Watlow, Hannibal, Mo.), resistive heaters (e.g., wire heaters), laser heaters (e.g., 48-series lasers, available from Synrad, Mukilteo, Wash., and C-Series lasers, available from Coherent®, Inc., Santa Clara, Calif.), and RF induction heaters.

Vibrators 225 can include one or more devices that are capable of vibrating plates 205 and 210. Examples of vibrators include ultrasonic transducers (available from Etalon, Indianapolis, Ind., and Finnsonic, Lahti, Finland), piezoelectric devices, magnetic resonators, particle bombardment devices, and vibration generators.

Motor 230 and/or motor 235 can include one or more devices capable of moving plates 205 and 210 in the directions described above. Examples of motors include servomotors (e.g., BSM N-Series servomotors, available from Baldor Electric Company, Fort Smith, Ark.), linear motors (e.g., BLMUC series linear motors, available from Aerotech, Inc., Pittsburgh, Pa.), rotary motors (e.g., BM series rotary motors, available from Aerotech, Inc., Pittsburgh, Pa.), stepper motors, and piezoelectric motors.

Support pin 215 can include one or more materials having sufficient rigidity and/or strength to support forces applied by plates 205 and 210. In some embodiments, support pin 215 includes one or more materials that have relatively high levels of thermal conductivity. Support pin 215 can, for example, include one or more materials that have a thermal conductivity of about 9.0 W/m-K or greater (e.g., about 9.0 W/m-K to about 400 W/m-K). In certain embodiments, support pin includes one or more materials that have a relatively high flexural strength (e.g., a flexural strength of about 100 MPa or more, about 100 MPa to about 900 MPa). Support pin 215 can, for example, include one or more metals, such as stainless steel, titanium, aluminum, PERSS, elgiloy, nitinol, hastalloy, and alloys including one or more of these materials. In certain embodiments, support pin 215 and plates 205 and 210 include the same material(s).

To bond waist portion 120 to inner member 112, waist portion 120 and inner member 112 are positioned between plates 205 and 210, as shown in FIG. 2, with a support pin 215 positioned within guidewire lumen 109 of inner member 112. Inner surfaces 209 and 214 of plates 205 and 210, respectively, can contact the outer surface of waist portion 120 in order to hold waist portion 120 and inner member 112 in place between plates 205 and 210. Waist portion 120 can have an outer diameter of about 0.5 millimeter to about 6.0 millimeters, and inner member 112 can have an inner diameter of about 0.4 millimeter to about 5.9 millimeters. Thus, plates 205 and 210, during use, can be separated by a distance of about 0.5 millimeter to about 6.0 millimeter. In some embodiments, plates 205 and 210 can be separated by up to about 100 millimeters. This relatively large separation distance can aid in positioning members between the plates and removing members from the between the plates. Support pin 215 can have an outer diameter of about 0.49 millimeter to about 5.9 millimeter.

While waist portion 120 and inner member 112 are positioned between plates 205 and 210, heaters 220, vibrators 225, and motors 230 can be activated to apply heat, vibratory energy, and pressure, respectively, to waist portion 120 via plates 205 and 210. As plates 205 and 210 are heated and vibrated, they transmit heat and vibratory energy to waist portion 120 in those areas in which plates 205 and 210 contact waist portion 120. The transmission of heat can cause the materials from which waist portion 120 and/or inner member 112 are formed to soften. It is believed that the vibratory energy provides short bursts of energy spikes, which can help to initiate the fusing process of the materials of waist portion 120 and inner member 112. The energy spikes can, for example, provide intermittent increases in pressure and temperature at points within waist portion 120 and/or inner member 112. Thus, the heat and vibratory energy can help to enhance the bond between waist portion 120 and inner member 112.

While plates 205 and 210 are being heated and vibrated, motor 230 moves plates 205 and 210 toward one another, which compresses waist portion 120 and inner member 112 between plates 205 and 210. The force applied to plates by motor 230 can, for example, compress one region of waist portion 120 and inner member 112 between plate 205 and support pin 215, and can compress an opposite region of waist portion 120 and inner member 112 between plate 210 and support pin 215. The compression of waist portion 120 and inner member 112 can help to bond the materials of waist portion 120 and inner member 112 to one another. Plates 205 and 210 can, for example, supply pressure sufficient to force waist portion 120 and inner member 112 together without substantially deforming waist portion 120 and inner member 112.

In addition, while the heat, vibratory energy, and pressure are being applied to waist portion 120, plates 205 and 210 are moved laterally relative to one another by motor 235. As a result, waist portion 120 and inner member 112 are moved (e.g., rolled) between plates 205 and 210. In certain embodiments, plates 205 and 210 can be moved back and forth in multiple cycles, which can cause waist portion 120 and inner member 112 to roll back and forth multiple times between plates 205 and 210. The rolling of waist portion 120 and inner member 112 between plates 205 and 210 can help to ensure that waist portion 120 and inner member 112 are bonded together about a majority (e.g., the entirety) of their inner and outer circumferential surfaces, respectively.

As a result of the bond created between waist portion 120 and inner member 112, waist portion 120 and inner member 112 can remain secured to one another during use of balloon catheter 100. The bond can, for example, be sufficient to withstand separation forces associated with inflating balloon 105 such that balloon 105 remains attached to catheter shaft assembly 110 during and after inflation of balloon 105.

The amount of heat, vibratory energy, and pressure applied to waist portion 120 and inner member 112 can depend on a number of factors, including the thickness of waist portion 120 and inner member 112 as well as the types of materials from which waist portion 120 and inner member 112 are formed. Furthermore, the level or intensity of each of the heat, vibratory energy, and pressure can be dependent upon one another. For example, the amount of heat applied can be dependent upon the amount of vibratory energy and pressure that is applied. The amount of heat applied can, for example, increase as the level of vibratory energy and/or pressure decreases, and vice versa. Similarly, the amount of vibratory energy applied can be dependent on the amount of heat and/or pressure being applied, and the amount of pressure applied can be dependent on the amount of heat and/or vibratory energy being applied. Time can be another factor. The intensity of the heat, vibratory energy, and pressure can generally decrease as the amount of time for which they are applied to waist portion 120 increases, and vice versa.

Figure 3:
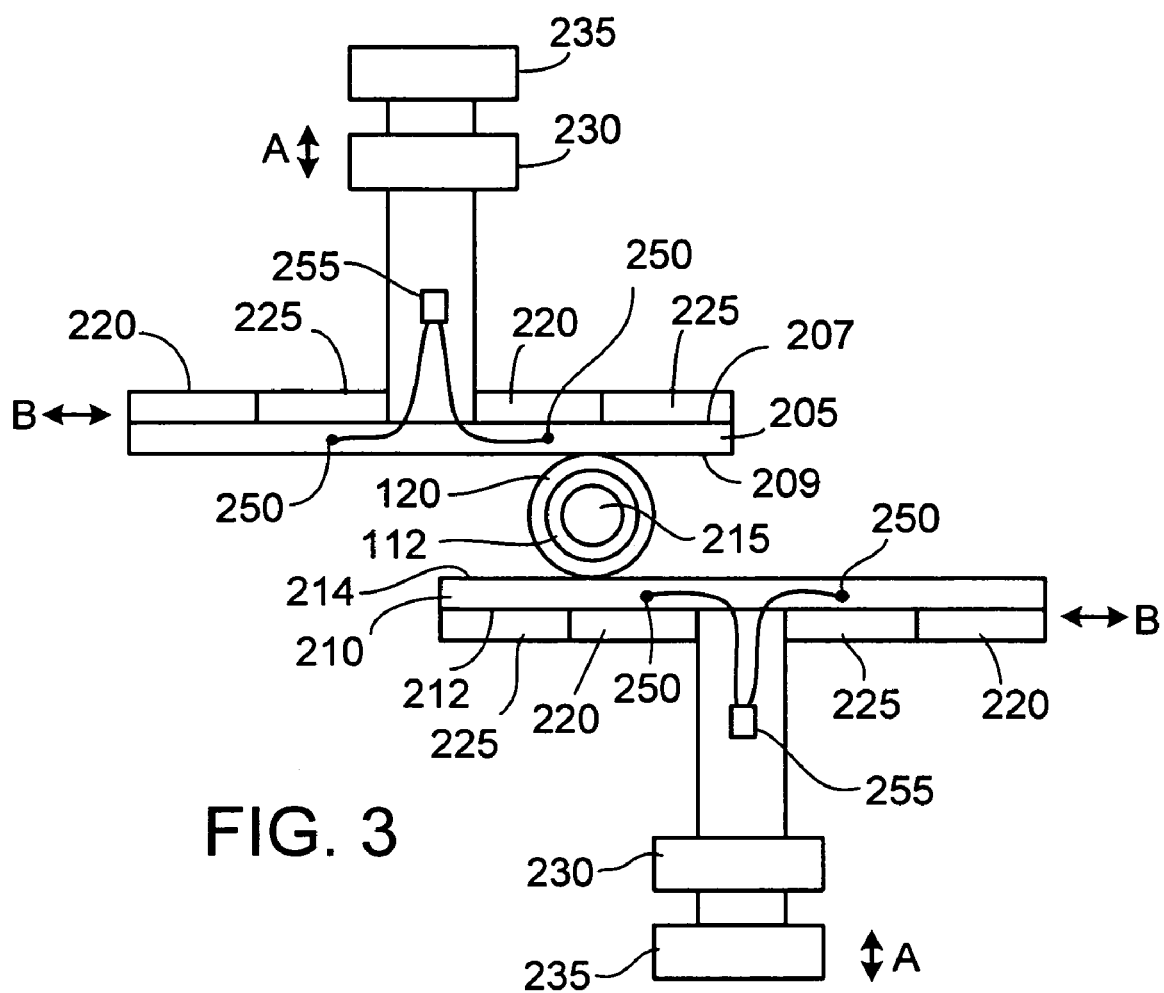
FIG. 3 illustrates an embodiment of a medical device manufacturing apparatus.

In certain embodiments, the bonding apparatus includes detectors that can detect the temperature of plates 205 and 210, the pressure exerted by plates 205 and 210, and/or the vibrations of plates 205 and 210. Referring to FIG. 3, for example, in some embodiments, plates 205 and 210 are equipped with thermocouples 250 that can measure the temperature of plates 205 and 210. Thermocouples 250 are connected to a control unit 255 that can control the output of heaters 220 and/or vibrators 225. As shown in FIG. 3, thermocouples 250 and control unit 255 are electrically connected by wires. However, thermocouples 250 can alternatively or additionally be connected to control unit 255 using other connections, including, for example, wireless connections. Control unit 255 can also be connected to heaters 220, vibrators 225, and/or motors 230 using one or more of these connection techniques. Control unit 255 can include one or more processors. Based on the detected temperature of plates 205 and 210, control unit 255 can adjust the heat output of heaters 220 and/or the vibratory energy of vibrators 225 to maintain waist portion 120 and/or inner member 112 at a desired temperature (e.g., a temperature below the melting temperature of the materials from which waist portion 120 and/or inner member 112 are formed). The pressure produced at motors 230 can also be adjusted.

The bonding apparatus can alternatively or additionally include a pressure sensor (not shown) and/or a vibration detector (not shown). The pressure sensor and/or vibration detector can be connected to control unit 255, such that the intensity of heat, vibratory energy, and pressure can be adjusted based on the measured pressure and/or vibration.

In some embodiments, waist portion 120 and inner member 112 are heated to a temperature that is less than the melting temperature of the materials from which waist portion 120 and inner member 112 are formed. Waist portion 120 and inner member 112 can, for example, be heated to a temperature that softens the materials from which they are formed without substantially melting those materials. In some embodiments, waist portion 120 and inner member 112 are heated to temperatures that are at least about one degree Celsius (e.g., about one to about 50 degrees Celsius) less than the respective melting points of waist portion 120 and inner member 112. In certain embodiments, waist portion 120 and/or inner member 112 are heated to a temperature of about 40 degrees Celsius to about 200 degrees Celsius. The temperature of plates 205 and 210 can be adjusted according to produce a desired temperature in waist portion 120. In some embodiments, plates 205 and 210 are heated to a temperature of about 200 degrees Celsius or less (e.g., about 174 degrees Celsius or less).

In certain embodiments, the vibratory energy applied to waist portion 120 and/or inner member 112 creates localized heating within waist portion 120 and/or inner member 112 that exceeds the melting temperature of materials from which waist portion 120 and/or inner member 112 are formed. The spikes of energy created by the vibrators can, for example, melt localized regions of material within waist portion 120 and/or inner member 112. In certain embodiments, the vibrators are configured such that the spikes of energy travel through waist portion 120 and through at least a portion of inner member 112. The localized melting within waist portion 120 and inner member 112 can help to fuse those materials together.

In some embodiments, the vibratory energy is transmitted at an ultrasonic frequency. However, other frequencies can alternatively or additionally be used. Plates 205 and 210 can transmit vibratory energy at a frequency of about 20 KHz to about 100 KHz (e.g., about 20 KHz to about 60 KHz, about 40 KHz to about 60 KHz).

Motor 230 can apply a force to plates 205 and 210 that is at least sufficient to join waist portion 120 and inner member 112 together. In some embodiments, motor 230 applies a force of about one gram to about 3 Kg (e.g., about 400 grams to about 1200 grams) to plates 205 and 210. The force applied by motor 230 can be transferred to waist portion 120 and/or inner member 112 as plates 205 and 210 press against opposite regions of waist portion 120. In some embodiments, the pressure applied to waist portion 120 and/or inner member 112 can be about one gram or greater (e.g., about 400 grams to about 1200 grams).

The amount of time for which the heat, vibratory energy, and/or pressure are applied to waist portion 120 is a function of the speed of the lateral movement of plates 205 and 210, the intensity of the heat, the intensity of the vibratory energy, and the intensity of the pressure. The heat, vibratory energy, and/ or pressure can be applied to waist portion 120 for about two seconds to about 120 seconds (e.g., about five seconds to about ten seconds). Upon completing the bonding process, waist portion 120 and inner member 112 are sufficiently bonded to withstand forces created by the inflation of balloon 105 to a predetermined pressure (e.g., about 200 psi or more, about 300 psi or more, about 230 psi to about 400 psi). The bond can, for example, prevent waist portion 120 and inner member 112 from becoming separated from one another when balloon 105 is inflated.

While several embodiments have been described above, other embodiments are possible.

As an example, while inner and outer members 112 and 114 have been described as including a polyester, such as Hytrel®, inner member 112 and/or outer member 114 can alternatively or additionally include one or more other materials. In some embodiments, inner member 112 and/or outer member 114 include one or more polymeric materials. Examples of materials from which inner member 112 and/or outer member 114 can be formed include polyolefins, polyamides, thermoplastic polyurethanes, and copolymers of these materials.

As another example, while balloon 105 has been described as including PET, balloon 105 can alternatively or additionally include one or more other materials. In certain embodiments, balloon 105 includes one or more polymeric materials. Examples of materials from which balloon 105 can be formed include polyethylene, polyvinyl chloride, Surlyne polyethylene ionomer copolymer, Pebax® polyamide-polyether-polyester block copolymer, PBT (polybutylene terephthalate), poly (butylene terephthalate)-block-poly (tetramethylene oxide), Arnitel®, Hytrel®, polyether etherketone (PEEK), Teflon®, polytetrafluoro-ethylene (PTFE), nylon (e.g., nylon 12), and their copolymers, as well as other polyolefins and silicone elastomers. Other balloon materials are disclosed in U.S. Pat. No. 6,242,063 and in PCT Publication WO 97/32624. As a further example, while the methods above describe laterally moving bonding plates 205 and 210 in order to roll waist portion 120 and inner member 112 between the plates, in certain embodiments, only one of the plates is moved laterally while the other plate remains fixed. Alternatively or additionally, the moveable plate can be positioned adjacent other flat, stationary surfaces to achieve a similar result. In some embodiments, the fixed surface (e.g., the stationary plate or the flat, stationary surface) is equipped with heaters and vibrators. However, the fixed surface can alternatively lack heaters and/or vibrators.

Figure 4:
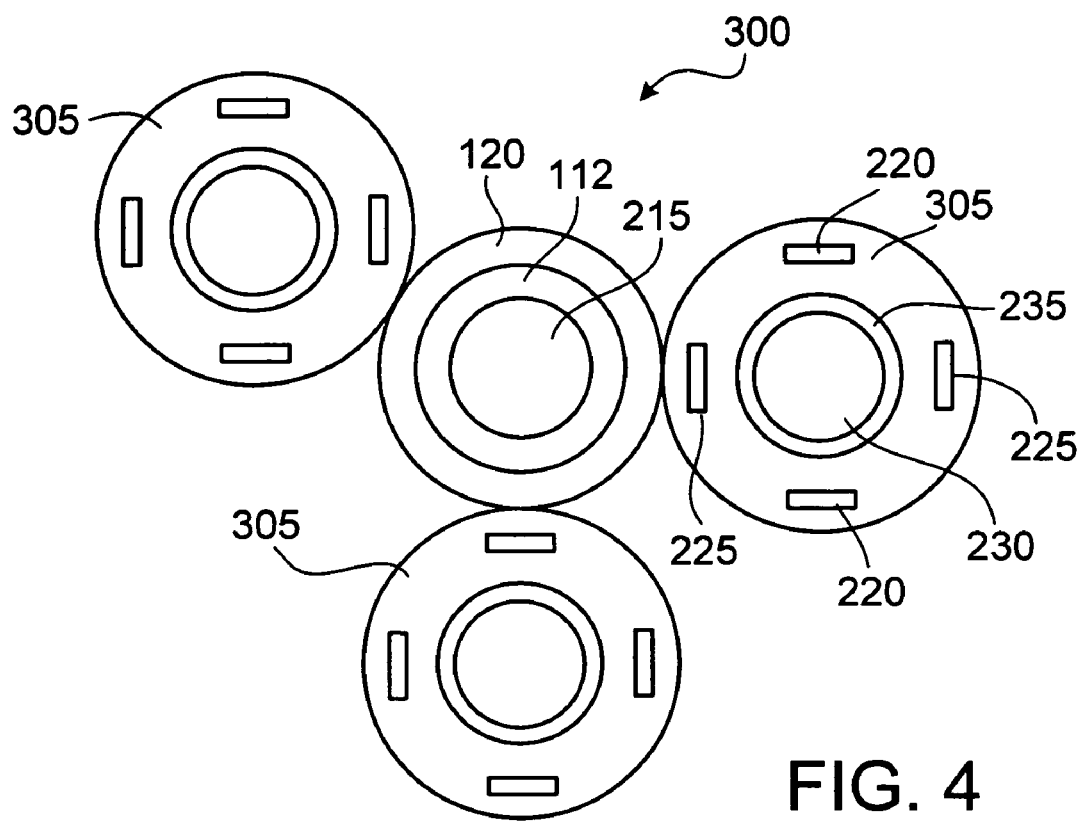
FIG. 4 illustrates an embodiment of a medical device manufacturing apparatus.

As an additional example, while the embodiments described above describe opposed plates that are configured to apply heat, vibratory energy, and/or pressure to waist portion 120 and/or inner member 112, other types of devices can alternatively or additionally be used. As shown in FIG. 4, for example, an apparatus 300 includes multiple rollers 305 arranged about a central region. Each of rollers 305 is equipped with multiple heaters 220 and vibrators 225. Rollers 305 are operatively connected to motors 230 via shafts (not shown), which can force rollers 305 toward the central region about which rollers 305 are arranged. Rollers 305 are also operatively connected to motors 235, which can rotate rollers 305 about their central axes. To bond waist portion 120 to inner member 112, the balloon catheter is positioned within the central region between the rollers. Rollers 305 can be positioned such that their outer surfaces are in contact with the outer surface of waist portion 120. This contact between the outer surfaces of rollers 305 and the outer surface of waist portion 120 can help to hold waist portion 120 and inner member 112 in place between rollers 305. When heaters 220 and vibrators 225 are activated, rollers 305 apply heat and vibratory energy to waist portion 120. Upon activating motor 230, waist portion 120 and inner member 112 are compressed between rollers 305. The combination of the heat, vibratory energy, and pressure applied to waist portion 120 can help to bond waist portion 120 to inner member 112. Motor 235 can also be activated so that rollers 305 rotate about their axes, which can cause waist portion 120 and inner member 112 to rotate about their axes. The rotation of waist portion 120 and inner member 112 can help to ensure a complete bond about the inner circumference of waist portion 120.

Figure 5:
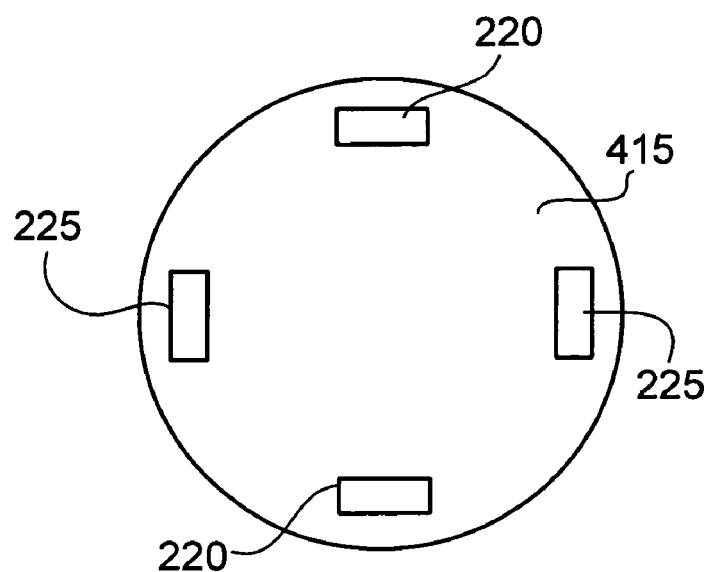
FIG. 5 illustrates a cross-sectional view of an embodiment of a support pin that can be used with the medical device manufacturing apparatus of FIGS. 2-4.

As an additional example, while heat, pressure, and vibratory energy have been described as being applied by plates 205 and 210 and rollers 305, heat, pressure, and/or vibratory energy can alternatively or additionally be applied by the support pin positioned within lumen 109 of inner member 112. FIG. 5 shows a support pin 415 that includes multiple heaters 220 and vibrators 225 arranged about its circumference. Support pin 415 can be used in a similar manner to support pin 215, which was discussed above. For example, support pin 415 can be placed in lumen 109 of inner member 112, and waist portion 120 and inner member 112 can be positioned between plates 205 and 210. The bonding process can be carried out as described above. However, in addition to applying heat and vibratory energy externally of waist portion 120 and inner member 112 via plates 205 and 210, heat and vibratory energy can also be applied from within waist portion 120 and inner member 112 via support pin 415. Thus, heat, vibratory energy, and/or pressure can be directly applied to both the waist portion 120 and inner member 112, which can help to enhance the bond between waist portion 120 and inner member 112. Applying heat, vibratory energy, and/or pressure to both waist portion 120 and inner member 112 can, for example, increase the speed with which waist portion 120 and inner member 112 are bonded to one another and can help to increase the bond strength between waist portion 120 and inner member 112.

While support pin 415 is described as including heaters 220 and vibrators 225, other arrangements are possible. For example, as an alternative to or in addition to heaters 220, support pin 415 can include a lumen that receives hot liquid (e.g., hot water) and/or hot gas (e.g., hot air). The hot liquid and/or hot gas can be forced through the lumen in order to heat support pin 415. The heat from support pin 415 can then be used to heat inner member 112, as described above. Similarly, while heaters 220 and vibrators 225 have been described as being positioned within support pin 415, heaters and/or transducers can alternatively or additionally be connected to an external portion of support pin 415 (e.g., to a portion of support pin 415 that extends outside of inner member 112).

As another example, while each of the plates and rollers of the embodiments described above include heaters and vibrators, it is also possible for some of the plates and rollers to be equipped with only heaters while others are equipped with only vibrators. Thus, some of the plates and rollers can function to heat waist portion 120, while others function to apply pressure to waist portion 120. Similarly, still other plates and rollers can be configured to apply vibratory energy to waist portion 120.

As an additional example, while many of the embodiments above involve heating waist portion 120 and/or inner member 112 by contacting waist portion 120 and/or inner member 112 with heated members (e.g., the plates and rollers), other techniques can be used. In some embodiments, the bonding apparatus includes a laser heater. The laser heater can be configured to direct laser energy onto waist portion 120 and/or inner member 112 as pressure and vibratory energy are being applied using any of the techniques described herein. An air heater is another type of heater that can be used for this purpose. Rather than directing laser energy to waist portion 120 and/or inner member 112, a stream of heated air can be directed to waist portion 120 and/or inner member 112. Other non-contact heating devices can similarly be used.

As a further example, while the embodiments above describe applying vibratory energy to waist portion 120 by contacting waist portion 120 with a vibrating member, other techniques can be used. In certain embodiments, vibratory energy is applied to waist portion 120 and inner member 112 by submerging waist portion 120 and inner member 112 along with the bonding apparatus in a fluid bath that is vibrated at a desired frequency. The fluid bath can include one or more gases and/or liquids. While vibrating the fluid, the medical device can be heated and/or can have pressure applied to it using techniques described herein in order to bond waist portion 120 to inner member 112.

As an additional example, in some embodiments, heat, vibratory energy, and pressure are applied to the medical device in a sequential fashion. In some embodiments, for example, waist portion 120 and/or inner member 112 are heated, and then pressure and vibratory energy are applied to them. Alternatively or additionally, the heat, vibratory pressure, and pressure can be sequentially applied in any other order.

As a further example, while the embodiments described above relate to bonding a waist portion of a medical balloon to a catheter shaft (e.g., inner and/or outer members 112 and 114 of catheter shaft assembly 110), the methods and apparatus described herein can alternatively or additionally be used to bond portions of other types of medical devices. For example, the methods and apparatus described herein can be used to bond a distal portion of a catheter shaft to a proximal portion of a catheter shaft and/or to bond an inner catheter shaft to an outer catheter shaft.

As another example, while pressure has been described as being applied to plates 205 and 210 by motors, other types of mechanisms can alternatively or additionally be used. In some embodiments, for example, the apparatus is equipped with a hand lever, such that the user can apply manual force to waist portion 120 and inner member 112 during the bonding process.

As an additional example, while embodiments above describe positioning support pin 215 within inner member 112 to provide support in an interior region of inner member 112, other techniques can be used to provide inner member 112 with support. In some embodiments, for example, a pressurized liquid and/or gas (e.g., pressurized air) is contained within one or more of the lumens of catheter shaft assembly 110. In certain embodiments, the lumens of catheter shaft assembly 110 can be pressurized to different levels.

As a further example, while the embodiments above involve applying heat, vibratory energy, and pressure to the medical device, in certain embodiments, only a subset of these energies are applied to the medical device. In certain embodiments, for example, heat and vibratory energy are applied to the medical device without applying pressure. For example, the portions of the medical device to be bonded can contact one another with the force of gravity alone. While contacting one another in this way, heat and vibratory energy can be applied to cause the two portions to bond together.

As an additional example, while the embodiments described above involve bonding two components of a medical device together, the methods and apparatus described herein can also be used to bond three or more components of a medical device together, sequentially or simultaneously.

As an additional example, while many of the embodiments above describe the bonding together of components including similar materials (e.g., polymeric materials), in some embodiments, the above-described methods can be used to bond components including different types of materials. A polymeric material can, for example, be bonded to a porous material, such as a ceramic material. During the bonding process, the energy can be applied to the ceramic component and/or to the polymeric component. The energy can soften the polymeric material and force some of the polymeric material into pores of the ceramic material. The techniques described above can similarly be used to bond a polymeric material to other types of porous materials.

Other embodiments are in the claims.

What is claimed is:

1. A method of manufacturing a medical device having a first portion and a second portion, the method comprising:
    contacting the first portion and the second portion at a contact area, at least one of the first and second portions of the medical device comprising one or more polymers;
    heating at least one of the first and second portions at the contact area by generating heat energy within a device and transferring that heat energy from the device to the at least one of the first and second portions at the contact area;
    vibrating at least one of the first and second portions at the contact area; and
    rolling the medical device whereby a rotational motion about a longitudinal axis of the medical device is imparted to the medical device during the heating and vibrating steps,
    wherein the method comprises positioning the medical device between two or more members, the two or more members being configured to transmit heat and vibratory energy to at least one of the first and second portions, wherein the rolling is performed by the two or more members.

2. The method of claim 1, wherein the heating and vibrating are performed simultaneously.

3. The method of claim 1, wherein the heating and vibrating are performed by a single device.

4. The method of claim 1, wherein the first and second portions are contacted by applying pressure to at least one of the first and second portions.

5. The method of claim 4, wherein the pressure is applied while heating and vibrating at least one of the first and second portions.

6. The method of claim 1, wherein the heating and vibrating are performed externally of the medical device.

7. The method of claim 1, wherein the method comprises applying at least one of heat and vibratory energy to the first portion, and applying at least one of heat and vibratory energy to the second portion.

8. The method of claim 7, further comprising applying pressure to at least one of the first and second portions.

9. The method of claim 1, wherein the medical device comprises a balloon catheter.

10. The method of claim 9, further comprising inserting a support member within a lumen defined by the balloon catheter.

11. The method of claim 1, wherein the method comprises positioning the medical device between two opposed members, at least one of the opposed members being configured to transmit at least one of heat and vibratory energy to at least one of the first and second portions.

12. The method of claim 1, wherein the method comprises contacting a member to the medical device, the member being configured to transmit at least one of heat and vibratory energy to at least one of the first and second portions.

13. The method of claim 1, wherein the vibrating step comprises applying vibratory energy to at least one of the first and second portions.

14. The method of claim 13, wherein the vibratory energy comprises ultrasonic energy.

15. The method of claim 1, wherein the first and second portions are heated to a temperature that is less than a melting temperature of the one or more polymers of the at least one of the first and second portions.

16. The method of claim 1, further comprising detecting a temperature of a member configured to heat at least one of the first and second portions.

17. The method of claim 16, wherein the heating step comprises applying heat to at least one of the first and second portions as a function of the detected temperature.

18. An apparatus for manufacturing a medical device, the apparatus comprising:
  a first member adapted to contact at least one of first and second medical device components, at least one of the first and second medical device components comprising one or more polymers, the first member configured to generate and transmit heat energy and vibratory energy to at least one of the first and second medical device components to bond the first and second medical device components to one another; and
  a second member, the first and second members being configured to receive the first and second medical device components within a gap defined between the first and second members such that the first and second medical device components are entirely on a first side of the first member and the first and second medical device components are entirely on a first side of the second member, whereby the first member and the second member are adapted to roll the medical device whereby a rotational motion is imparted to the medical device.

19. The apparatus of claim 18, wherein the second member is configured to transmit at least one of heat, pressure, and vibratory energy to at least one of the first and second medical device components when the first and second medical device components are disposed within the gap.

20. The method of claim 11, wherein the two opposed members are plates each having a flat surface configured to contact the medical device.

21. The method of claim 11, whereby the rotational motion is imparted to the medical device by using the two opposed members to roll the medical device.

22. The method of claim 1, wherein the method comprises positioning the medical device between a plurality of rollers, at least one of the rollers being configured to transmit at least one of heat and vibratory energy to at least one of the first and second portions.

23. The method of claim 1, wherein the first member is a tubular member and wherein the second member is a tubular member disposed at least partially within the first member and wherein the method comprises forming a circumferential bond between the first and second members.

* * * * *